(12) United States Patent
Nakano et al.

(10) Patent No.: US 7,056,276 B2
(45) Date of Patent: Jun. 6, 2006

(54) CATHETER FOR RADIATION THERAPY

(75) Inventors: Ryoji Nakano, Settsu (JP); Takuya Ishibashi, Ikoma (JP)

(73) Assignee: Kaneka Corporation, Osaka (JP)

( * ) Notice: Subject to any disclaimer, the term of this patent is extended or adjusted under 35 U.S.C. 154(b) by 476 days.

(21) Appl. No.: 10/333,051

(22) PCT Filed: Jun. 15, 2001

(86) PCT No.: PCT/JP01/05155

§ 371 (c)(1),
(2), (4) Date: Jan. 14, 2003

(87) PCT Pub. No.: WO02/11805

PCT Pub. Date: Feb. 14, 2002

(65) Prior Publication Data

US 2003/0176758 A1  Sep. 18, 2003

(30) Foreign Application Priority Data

Aug. 2, 2000  (JP) .............................. 2000-234526

(51) Int. Cl.
*A61N 5/00* (2006.01)
(52) U.S. Cl. .......................................................... 600/3
(58) Field of Classification Search ................ 600/1–8; 604/96, 101

See application file for complete search history.

(56) References Cited

U.S. PATENT DOCUMENTS

| | | | |
|---|---|---|---|
| 5,618,266 A | 4/1997 | Liprie | |
| 5,851,171 A * | 12/1998 | Gasson | 600/3 |
| 5,938,582 A * | 8/1999 | Ciamacco et al. | 600/3 |
| 5,947,924 A | 9/1999 | Liprie | |
| 6,416,457 B1 * | 7/2002 | Urick et al. | 600/3 |
| 6,450,988 B1 * | 9/2002 | Bradshaw | 604/96.01 |

FOREIGN PATENT DOCUMENTS

| | | |
|---|---|---|
| CA | 2242996 | 3/1999 |
| EP | 0904798 A1 | 3/1999 |
| JP | 59-181125 | 10/1984 |
| JP | 5-051356 | 7/1993 |
| JP | 10-179751 | 7/1998 |
| JP | 10-509332 | 9/1998 |
| JP | 11-114077 | 4/1999 |
| WO | WO 96/10436 | 4/1996 |

* cited by examiner

*Primary Examiner*—John P. Lacyk
(74) *Attorney, Agent, or Firm*—Hogan & Hartson LLP

(57) ABSTRACT

In an expandable part positioned on the tip end side of the catheter, protruding parts are produced in specific regions when the expandable part is expanded through the difference in elasticity between two materials having a different elasticity to one another. The structure is made to be such that low-elasticity regions and high-elasticity regions are disposed in the expandable part, and when pressure is applied the high-elasticity regions expand more than the low-elasticity regions, thus becoming the protruding parts. Alternatively, the structure is made to be such that two materials having a different elasticity to one another are made into a two-layer structure of an inner layer and an outer layer, and voids are provided in the layer formed from the low-elasticity material, so that when pressure is applied, parts of the layer formed from the high-elasticity material corresponding to the void parts become the protruding parts.

12 Claims, 6 Drawing Sheets

CATHETER FOR RADIATION THERAPY

TECHNICAL FIELD

The present invention relates to a catheter for radiation therapy for treating part of a body vessel with ionizing radiation.

BACKGROUND ART

A widely carried out therapy for stenosis of blood vessels, in particular stenosis of the coronary artery, which is a cause of myocardial infarction, angina pectoris and so on, is to expand the stenosed part using a catheter having a balloon disposed on the tip thereof, which is known as a PTCA (percutaneous transluminal coronary angioplasty) balloon catheter. Describing this technique in more detail, first a hollow $\phi 2$ mm to $\phi 3$ mm catheter called a guiding catheter for leading in the PTCA balloon catheter is led into the aorta, and the tip thereof is disposed at the entrance of the coronary artery. Next, a wire of outside diameter $\phi 0.010''$ (0.254 mm) to 0.018'' (0.457 mm) which is called a guide wire and fulfills a role of guiding the PTCA balloon catheter is led into the guiding catheter, and is passed through the stenosed part of the coronary artery. Then, the PTCA balloon catheter having the balloon disposed on the tip thereof is led in along the guide wire as far as the coronary artery, is similarly passed through the stenosed part, and the balloon part of the PTCA balloon catheter is disposed in the stenosed part. The balloon is then expanded using high-pressure physiological saline, contrast medium or the like, thus forcibly opening up the stenosed part.

However, there is a large problem with this PTCA therapy in that after the therapy, restenosis, i.e. repeated stenosis, occurs with a probability of approximately 40% within a short time period of 3 to 6 months. It has been shown that restenosis is caused by the blood vessel walls being damaged through the forcible expansion of the blood vessel by the balloon, and then smooth muscle cells proliferating excessively during the subsequent healing process.

As a countermeasure for this problem, it has been found that the incidence rate of restenosis can be reduced to 20% or less by leaving behind a metal tube called a stent after the balloon expansion, but from a clinical perspective there is an urgent need to further reduce this figure.

Recently, in Europe and America there has thus been progress in the clinical application of intravascular radiation therapy as a restenosis prevention method, and the results thereof have attracted attention. In some clinical trials, the results have been that the probability of restenosis occurring could be reduced down to approximately 7%. It is said that the reason for this is that if a suitable dose of radiation is irradiated onto the lesioned part after the balloon expansion, then cell proliferation during the healing process can be inhibited.

Currently, as a therapy system used in this application, there is a catheter system for intravascular radiation therapy. This is used after the expansion of the lesioned part using a PTCA balloon catheter, or after the placement of a stent. More specifically, after the PTCA treatment, the PTCA balloon catheter is pulled out of the body, and then a catheter for intravascular radiation therapy having a hollow tubular shaft sealed at the tip is led in as far as the lesioned part. As disclosed in U.S. Pat. No. 5,199,939, a wire having a radiation source at the tip thereof (a radioactive wire) is then passed through the lumen of the tubular shaft having the sealed tip, and is led as far as the lesioned part, and then radiation is irradiated from the radiation source for the required time. In general, a dose of approximately 20 to 30 Gy is irradiated. After the irradiation has been completed, the radioactive wire is pulled out of the body (withdrawn), and then the catheter for intravascular radiation therapy is also pulled out of the body, thus completing the therapy. In general, the leading in and withdrawal of a radioactive wire are carried out through remote automatic operation of a remote loader/unloader to prevent the surgeon from being exposed to radiation, with this often being done in the field of cancer therapy in particular. There are disclosures regarding this in U.S. Pat. No. 5,199,939, U.S. Pat. No. 5,302,168, U.S. Pat. No. 5,213,561, Published Japanese Translation of PCT Application No. 10-507951, and so on.

In recent clinical application, awareness has become great of the necessity of irradiating the blood vessel walls uniformly, and the necessity of securing blood flow from the proximal side to the distal side (peripheral side) during the therapy or during the irradiation, i.e. the necessity of a perfusion mechanism. Regarding irradiating the blood vessel walls uniformly, if the radiation source shifts away from the center of the blood vessel cross section when the radiation source is positioned at the lesioned part in the blood vessel, then the blood vessel wall that is too close to the radiation source will be irradiated excessively, resulting in necrosis of the blood vessel, an aneurysm or the like. Conversely, a dose of radiation sufficient for inhibiting smooth muscle proliferation will not reach the blood vessel wall far from the radiation source. The reason for this is that the energy of the radiation irradiated from the radiation source drops with distance from the radiation source. In the catheter system for intravascular radiation therapy, a mechanism is thus required that enables the blood vessel walls to be irradiated with a uniform dose by having a so-called centering function of positioning the radiation source in the center of the blood vessel cross section or the center of the cross section at the stenosed part.

Regarding the other requirement of securing blood flow to the distal side (peripheral side) blood vessels, i.e. the necessity of a perfusion mechanism, the required irradiation time is long, being approximately 5 to 10 minutes in the case that the radiation used is $\beta$-rays, and approximately 10 to 30 minutes in the case that the radiation used is $\gamma$-rays. In the case that such a long time is required as the irradiation time, if the coronary artery blood were not to flow to the peripheral coronary artery blood vessels during the irradiation, then the myocardial cells in peripheral parts would become ischemic, causing serious symptoms such as angina. A mechanism that allows blood to flow to the peripheral blood vessels at all times while irradiating the radiation and while carrying out centering during the irradiation, i.e. a perfusion mechanism, is thus required in the catheter system for intravascular radiation therapy.

Regarding the above, Published Japanese Translation of PCT Application No. 9-507783 discloses a number of mechanisms that simultaneously realize a centering function and a perfusion function. One such centering mechanism consists of spiral lobes, in which a balloon is disposed wound around a catheter tube in a spiral fashion. The radiation source is led in as far as the tip of the catheter shaft, and then the spiral balloon is expanded, whereby the radiation source can be positioned approximately in the center of the blood vessel cross section. Moreover, due to the spiral shape of the spiral balloon, during expansion blood is fed through the grooves from the proximal side to the distal side of the balloon.

However, in the case of these spiral lobes (the spiral balloon), unless special measures are adopted, problems and inconveniences such as the following arise.

A first problem is that if the thickness of the balloon is constant in the circumferential direction after molding, then in the balloon's natural expanded state, the balloon will not be a spiral shape, but rather will be a straight shape. Consequently, when one attempts to wind the balloon in a spiral fashion around the catheter shaft and fix the balloon using an adhesive or the like, the balloon tries to return to its natural straight shape, and hence the fixing of the balloon in a certain position on the surface of the catheter shaft is difficult, i.e. there is a difficulty in terms of fixing the balloon precisely in position, and hence reproducibility is poor. This is a big disadvantage from a manufacturing perspective in particular in the case of using an adhesive having a long hardening time. Moreover, if the spiral balloon is not fixed precisely in position, i.e. if places exist where the groove width is too large, then the precision of the centering will tend to become poor, which is a serious problem from a clinical perspective.

A second problem is that when fixing the straight balloon onto the catheter shaft such that the balloon goes into a spiral state, it is necessary to twist the balloon slightly forcibly. Due to reaction, stress thus arises in the balloon such as to twist the shaft back. With a catheter for intravascular radiation therapy, a radiation source wire passes through (is delivered through) the lumen of the catheter; if the shaft is twisted, then the shaft lumen will deform, and hence there will be resistance when the radiation source passes through the catheter lumen, or in the worst cases the radiation source will not pass through the catheter lumen. In such a case, the time for which the radiation source is in the twisted part of the shaft will become long, and hence the patient's exposure to radiation at this part will increase, which is not only a large problem in terms of safety, but moreover it will no longer be possible to irradiate the region to be treated with radiation effectively.

A third problem is that when the balloon has been expanded, there will be a large stress in the balloon due to trying to return to the natural straight state, and in the case that the expansion pressure is high, there will be a risk of the balloon dropping off the shaft due to this stress. These may be serious problems from a clinical perspective.

A fourth problem is that before the balloon is expanded, and when the balloon has been expanded and then contracted, there are large level differences on the outer surface. In particular, the level differences on the balloon part after the balloon has been expanded and then contracted are marked, resulting in a large resistance when moving through a blood vessel. Moreover, in the worst cases, the inside of the blood vessel may be damaged.

Moreover, Japanese Patent Application Laid-open No. 10-179751 also discloses a number of mechanisms that simultaneously realize a centering function and a perfusion function. As the centering mechanism, there is a centering balloon that has at least two expandable spokes, and this is installed on the outer surface near to the tip of the catheter. By expanding the centering balloon symmetrically, a radiation source disposed in the catheter is centered in a blood vessel. However, problems and inconveniences such as the following arise with the structure disclosed in Japanese Patent Application Laid-open No. 10-179751.

A first problem is that the shape of the centering balloon consists of spokes that are long in the axial direction; when the centering balloon is expanded, the balloon tries to return to its natural straight shape, and hence this part becomes rod-like and hard. In the case for example that the lesioned part to be treated is an extremely curved blood vessel, the balloon may lose out to the curvature of the blood vessel and may thus not expand sufficiently to realize perfusion, and moreover the blood vessel may be irradiated excessively with radiation at the part where the balloon has not expanded sufficiently, which may cause necrosis of the blood vessel, an aneurysm or the like. Moreover, the centering balloons, two or more of which are provided as described above, will not expand uniformly, and hence it will not be possible to realize the centering of the radiation source, and as a result part of the lesioned region to be treated may be irradiated excessively with radiation, which may cause necrosis of the blood vessel, an aneurysm or the like. Furthermore, upon expanding the centering balloon, a force acts to straighten out the curved blood vessel, and with a peripheral blood vessel in particular the blood vessel may be damaged.

A second problem is that because a centering balloon having at least two expandable spokes is installed on the outer surface close to the tip of the catheter, even before expansion, the structure is such that there are large level differences on the outer surface of the balloon. The catheter must proceed along a narrow, curved blood vessel as far as the region to be treated, but if there are large level differences around the catheter, then the ability of the surgeon to maneuver the catheter will be impaired, and it may not be possible to dispose the catheter in the region to be treated, and moreover the inside of the blood vessel may be damaged by the level differences. Furthermore, when the pressure is reduced and the centering balloon is contracted after having been expanded, then the state becomes such that the balloon sticks outwards in wing shapes, i.e. such that there are yet bigger level differences on the outer surface of the balloon, and hence there will be a large resistance when moving through the blood vessel. Moreover, in the worst cases, the inside of the blood vessel may be damaged.

DISCLOSURE OF THE INVENTION

It is an object of the present invention to provide a catheter for radiation therapy according to which the problems described above can be avoided or reduced. That is, it is an object of the present invention to provide a catheter for radiation therapy that has a centering mechanism that enables blood vessel walls to be irradiated with a uniform radiation dose, and has a perfusion mechanism that allows blood to flow to peripheral blood vessels at all times during centering, and for which there are no undulations on the surface of the catheter when the catheter is being moved through a blood vessel, and hence there is little resistance to movement through the blood vessel, and there is no risk of the inner surface of the blood vessel being damaged, and moreover for which manufacture is easy.

To resolve the above problems, the present invention relates to a catheter for radiation therapy for treating part of a body vessel with ionizing radiation, the catheter for radiation therapy having a long catheter having a tip end part and a base end part, and characterized by comprising an expandable part positioned on the tip end side of the catheter, and means for passing a radiation source through the catheter in a longitudinal direction to dispose the radiation source in the expandable part, wherein the expandable part has a two-layer structure in a radial direction of an inner layer and an outer layer, at least the inner layer is formed from an elastic substance, the bend elastic constant as measured using a measurement method based on ASTM-D790 is set to be at least 20% higher for the outer layer than for the inner layer, one or a plurality of voids are present in the outer layer, the expandable part has no protruding parts on the surface thereof when not expanded, and parts of the inner layer protrude from the voids of the outer layer when the expandable part is expanded, whereby when the expandable part is expanded, perfusion of a body fluid in the vicinity of the expandable part is made possible, and the protruding parts of the expandable part are disposed such that, when a radiation source is disposed inside the expandable part, the radiation source is always positioned in the center of the expandable part in the radial direction.

Moreover, as another means, the present invention relates to a catheter for radiation therapy for treating part of a body vessel with ionizing radiation, the catheter for radiation therapy having a long catheter having a tip end part and a base end part, and being characterized by comprising an expandable part positioned on the tip end side of the catheter, and means for passing a radiation source through the catheter in a longitudinal direction to dispose the radiation source in the expandable part, wherein the expandable part has high-elasticity regions and low-elasticity regions, the bend elastic constant as measured using a measurement method based on ASTM-D790 is set to be at least 20% higher for the low-elasticity regions than for the high-elasticity regions, the expandable part has no protruding parts on the surface thereof when not expanded, and one or a plurality of protruding parts are produced at the high-elasticity regions when the expandable part is expanded, whereby when the expandable part is expanded, perfusion of a body fluid in the vicinity of the expandable part is made possible, and the protruding parts of the expandable part are disposed such that, when a radiation source is disposed inside the expandable part, the radiation source is always positioned in the center of the expandable part in the radial direction.

Moreover, as yet another means, the present invention relates to a catheter for radiation therapy for treating part of a body vessel with ionizing radiation, the catheter for radiation therapy having a long catheter having a tip end part and a base end part, and being characterized by comprising an expandable part positioned on the tip end side of the catheter, and means for passing a radiation source through the catheter in a longitudinal direction to dispose the radiation source in the expandable part, wherein the expandable part has a two-layer structure in a radial direction of an inner layer and an outer layer both formed from an elastic substance, the bend elastic constant as measured using a measurement method based on ASTM-D790 is set to be at least 20% higher for the inner layer than for the outer layer, one or a plurality of voids are present in the inner layer, the expandable part has no protruding parts on the surface thereof when not expanded, and parts of the outer layer corresponding to parts where the voids are present in the inner layer protrude when the expandable part is expanded, whereby when the expandable part is expanded, perfusion of a body fluid in the vicinity of the expandable part is made possible, and the protruding parts of the expandable part are disposed such that, when a radiation source is disposed inside the expandable part, the radiation source is always positioned in the center of the expandable part in the radial direction.

Here, in the present invention, ionizing radiation means radiation having an action of ionizing atoms in a substance upon passing through the substance, and is a concept that includes at least β-rays and γ-rays.

The catheter for radiation therapy according to the present invention has a tubular cavity for a guide wire that leads the catheter to the region to be treated. This guide wire tubular cavity may be provided along the whole length of the catheter, or may be provided not along the whole length of the catheter but rather in only part of the catheter in the axial direction. In the case that the guide wire tubular cavity is provided in only part of the catheter, a structure in which the guide wire tubular cavity is provided only within a 10 mm length from the tip end of the catheter on the tip end side relative to the expandable part is preferable. In the case of a structure in which the guide wire tubular cavity is provided along the whole length of the catheter, the guide wire is protected along the whole length of the catheter, and hence there is a characteristic feature that maneuvers carried out and forces applied at the part of the catheter held in the hand are readily transmitted to the tip end. Conversely, in the case of a structure in which the guide wire tubular cavity is provided in only part of the catheter, in particular in the case of a structure in which the guide wire tubular cavity is provided only within a 10 mm length from the tip end of the catheter on the tip end side relative to the expandable part, there is an advantage that the catheter can be made thin in the part where the guide wire tubular cavity is not provided, and hence the maneuverability of the catheter is improved, and the risk of the inside of a blood vessel being damaged when the catheter is led to the region to be treated is reduced.

With one means of the catheter for radiation therapy according to the present invention, the expandable part positioned on the tip end side has high-elasticity regions and low-elasticity regions, the bend elastic constant as measured using a measurement method based on ASTM-D790 is set to be at least 20% higher for the low-elasticity regions than for the high-elasticity regions, one or a plurality of voids are present in parts of the outer layer, the expandable part has no protruding parts on the surface thereof when not expanded, and parts of the inner layer protrude from the voids of the outer layer when the expandable part is expanded. Here, 'high-elasticity' is defined as a property whereby in general a large elastic deformation can be achieved, i.e. means the property of a substance for which in practice the amount of deformation in response to an applied force is large. Moreover, 'low-elasticity' is defined as the opposite property to high-elasticity. Furthermore, 'elastic constant' is defined as $\sigma/e$ for when the elastic strain e is proportional to the corresponding stress $\sigma$. Consequently, high elastic constant and low elasticity have the same meaning, and low elastic constant and high elasticity have the same meaning. With the present invention, taking the value of the bend elastic constant of the high-elasticity substance or high-elasticity regions as measured using a measurement method based on ASTM-D790 to be a, and taking the value of the bend elastic constant of the low-elasticity substance or low-elasticity regions as measured using a measurement method based on ASTM-D790 to be b, the relationship $b/a \geq 1.2$ holds. The above-mentioned protruding parts have as an objective thereof making perfusion of a body fluid possible, and moreover positioning in the center in the radial direction a radiation source that has been disposed inside the expandable part; the materials of the inner and outer layers, the thicknesses of the inner and outer layers, and the number, size, shape and pattern of arrangement of the voids in the outer layer can be selected as desired so long as this objective is realized. Preferably, the outside diameter expansion rate per unit expansion pressure is at least 25.0%/atm (0.247%/kPa) in regions where protruding parts are produced, and not more than 2.5%/atm (0.0247%/kPa) in regions where protruding parts are not produced; in this case, it is possible to maintain sufficient biological perfusion at a low pressure from 1 atm (1.013×10⁵ Pa) to 3 atm (3.040×10⁵ Pa) (gauge pressure) that is easy for a surgeon to handle. Hereinafter, all pressures in the present invention are expressed as gauge pressures.

With another means of the catheter for radiation therapy according to the present invention, the expandable part positioned on the tip end side has high-elasticity regions and low-elasticity regions, the bend elastic constant as measured using a measurement method based on ASTM-D790 is set to be at least 20% higher for the low-elasticity regions than for the high-elasticity regions, the expandable part has no protruding parts on the surface thereof when not expanded, and protruding parts are produced through the difference in elasticity when the expandable part is expanded. The protruding parts have as an objective thereof making perfusion of a body fluid possible, and moreover positioning in the center in the radial direction a radiation source that has been disposed inside the expandable part; the material, thickness, number, size, shape and pattern of arrangement of the relatively-high-elasticity regions can be selected as desired so long as this objective is realized, and moreover the size, shape and pattern of arrangement of the relatively-low-elasticity regions can be selected as desired so long as this objective is realized. Preferably, the outside diameter expansion rate per unit expansion pressure is at least 25.0%/atm (0.247%/kPa) in regions where protruding parts are produced, and not more than 2.5%/atm (0.0247%/kPa) in regions where protruding parts are not produced; in this case, it is possible to maintain sufficient biological perfusion at a low pressure from 1 atm (1.013×10⁵ Pa) to 3 atm (3.040×10⁵ Pa) that is easy for a surgeon to handle.

With yet another means of the catheter for radiation therapy according to the present invention, the expandable part positioned on the tip end side has a two-layer structure in a radial direction of an inner layer and an outer layer both formed from an elastic substance, the bend elastic constant as measured using a measurement method based on ASTM-D790 is set to be at least 20% higher for the inner layer than for the outer layer, one or a plurality of voids are present in parts of the inner layer, the expandable part has no protruding parts on the surface thereof when not expanded, and parts of the outer layer corresponding to parts where the voids are present in the inner layer protrude when the expandable part is expanded. The protruding parts have as an objective thereof making perfusion of a body fluid possible, and moreover positioning in the center in the radial direction a radiation source that has been disposed inside the expandable part; the number, size, shape and pattern of arrangement of the voids in the inner layer can be selected as desired so long as this objective is realized. Preferably, the outside diameter expansion rate per unit expansion pressure is at least 25.0%/atm (0.247%/kPa) in regions where protruding parts are produced, and not more than 2.5%/atm (0.0247%/kPa) in regions where protruding parts are not produced; in this case, it is possible to maintain sufficient biological perfusion at a low pressure from 1 atm (1.013× 10⁵ Pa) to 3 atm (3.040×10⁵ Pa) that is easy for a surgeon to handle.

Non-radiation-transmitting marking can be provided on the catheter according to the present invention; in this case, it is possible for a surgeon to proceed with an operation while gaining a precise understanding of the position of the catheter through the transmission of X-rays. The non-radiation-transmitting marking can be provided at both ends of one or a plurality of expandable parts, or can be provided as appropriate on a series of expandable parts.

The expandable part positioned on the tip end side of the catheter is led in to the region to be treated, and then the expandable part is expanded, whereby the expandable part protrudes out at a plurality of places, and body fluid flows between the protruding parts, and hence perfusion of the body fluid is ensured. Moreover, a radiation source is centered in the radial direction of the blood vessel walls by the protruding parts, and hence irradiation of the blood vessel walls with a uniform dose is ensured. After the expandable part has been expanded, one or a plurality of radiation sources are positioned in the region to be treated. Once a prescribed time period has passed, the radiation source(s) is/are pulled out, and then the expandable part is contracted, and the catheter is pulled out from the body.

It is preferable for the radiation source tubular cavity to be closed on the tip end side of the catheter, so that in the case that the radiation source separates away for some reason, the radiation source does not remain behind in the body vessel, and so that the radiation source does not come into contact with body fluid.

Any of various types of radiation source that have been publicly known from hitherto can be used as the radiation source; examples include phosphorus 32, cobalt 57, cobalt 60, krypton 85, strontium 89, strontium 90, yttrium 90, zirconium 95, technetium 99 m, palladium 103, ruthenium 106, iodine 125, iodine 131, cesium 137, barium 140, cerium 144, promethium 147, iridium 192, and gold 198, but there is no limitation to these.

Regarding the materials of the expandable part, polyurethanes, urethane type elastomers, polyamides, polyamide type elastomers, polyester type resins, polyester elastomers, olefin type resins, olefin type elastomers, polystyrene, styrene type elastomers, vinyl chloride, vinyl chloride type elastomers, silicones, natural rubber, and synthetic rubbers can be envisaged, but there is no limitation to these materials.

Moreover, the material of the outer layer of the expandable part may be a metal, with examples of this metal including stainless steels and titanium alloys that are used in medical instruments.

BEST MODE FOR CARRYING OUT THE INVENTION

Following is a description of various embodiments of the catheter according to the present invention with reference to the drawings.

Figure 1:
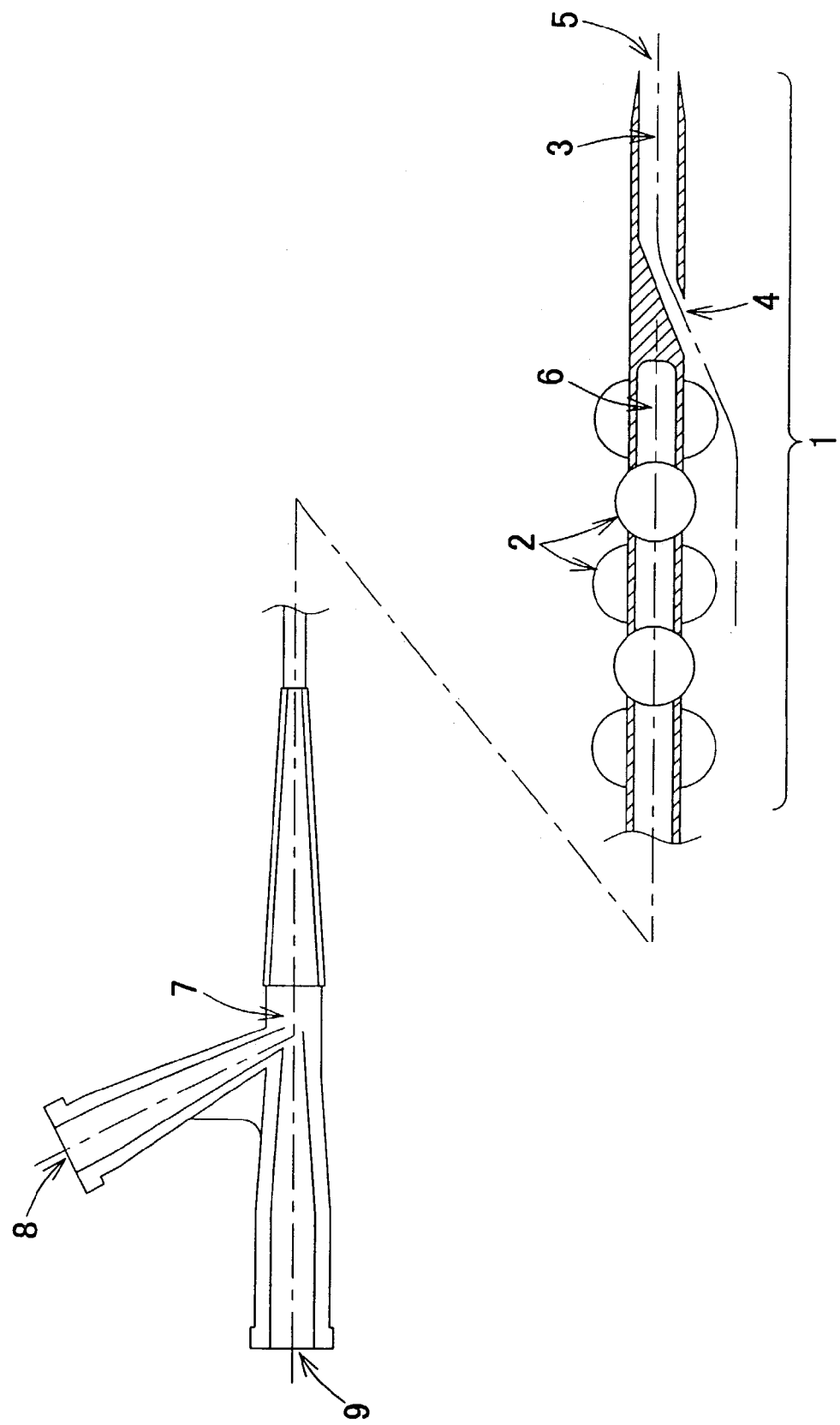
FIG. 1 is an axial direction sectional view of a first example.

A first example of FIG. 1 is a catheter for radiation therapy for treating part of a body vessel with ionizing radiation; a state in which the expandable part has been expanded is shown. The expandable part 1 of the catheter is positioned on the tip end side of the catheter, and in the expanded state has a plurality of protruding parts 2. Specifically, when the expandable part 1 is expanded, a plurality of pairs of protruding parts 2 are produced, with the protruding parts 2 that constitute each pair being disposed so as to be produced facing in opposite directions to one another in a direction orthogonal to the axial direction of the expandable part 1, and moreover with pairs of protruding parts 2 that are adjacent to one another in the axial direction being disposed close to one another with an angle of 90° therebetween in the circumferential direction. In the example shown in the drawing, there are five pairs of protruding parts 2 in succession in the axial direction with angles of 90° between adjacent pairs, and hence the catheter of the first example has a total of ten protruding parts 2. Moreover, the outline of each of the protruding parts as viewed from the direction of protrusion of the protruding part is approximately circular. In other words, the shape of each of the protruding parts 2 as viewed from the perpendicular direction of the protruding part 2 in the radial direction is approximately circular. Through the protruding parts 2, even in the case of a curved body vessel, a radiation source tubular cavity 6 is disposed in the center of the body vessel at all times, and hence irradiation can be carried out with a uniform dose.

Figure 2:
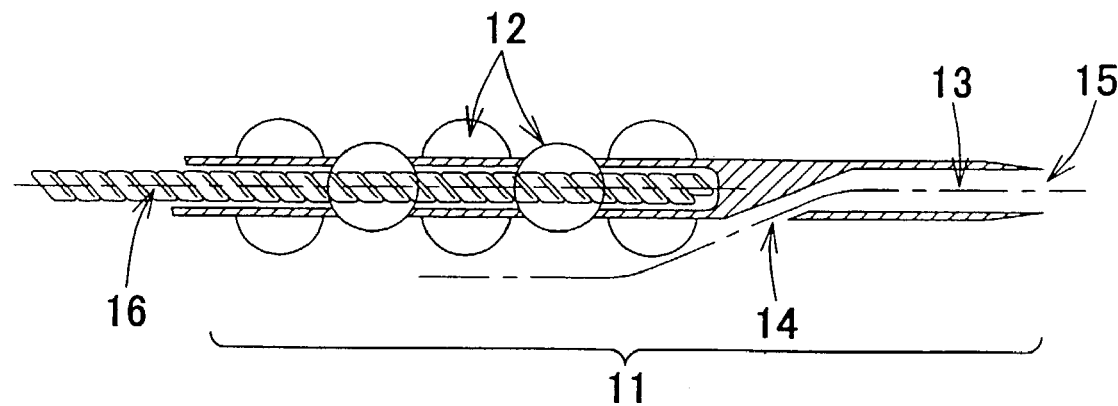
FIG. 2 shows a state in which a radiation source has been disposed in the case of the first example.
Figure 3:
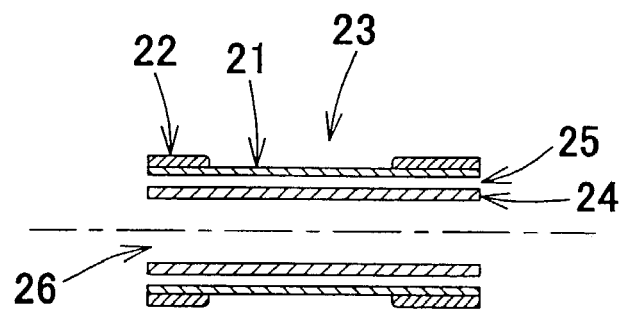
FIG. 3 shows the expandable part before expansion in the case of the first example.
Figure 4:
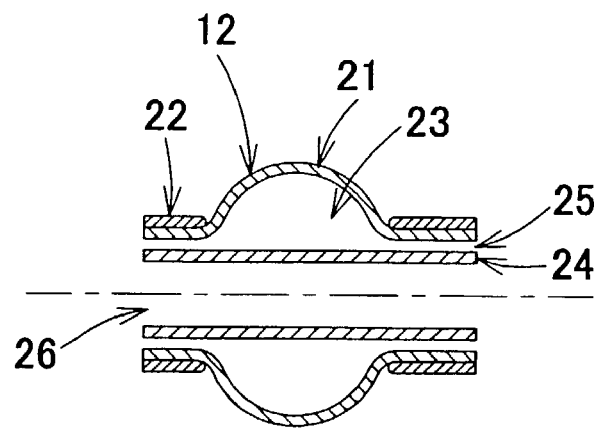
FIG. 4 shows the expandable part after expansion in the case of the first example.

The catheter has a guide wire tubular cavity 3, which is provided between a guide wire entrance part 4 and a guide wire exit part 5, with the guide wire entrance part 4 and the guide wire exit part 5 both being positioned on the tip end side relative to the expandable part 1. A manifold 7 is provided at a base end part of the catheter, and has an inflation port 8 and a radiation source port 9. The inflation port 8 communicates with the expandable part 1, and upon a surgeon carrying out an operation of introducing a contrast medium, physiological saline or the like from the inflation port 8 into the expandable part 1 to apply pressure, the protruding parts 2 are produced on the expandable part 1. Note that when the expandable part 1 is contracted, the inflation port 8 becomes a deflation port. The radiation source port 9 communicates with the radiation source tubular cavity 6; a radiation source 16 is inserted from the radiation source port 9 and is disposed inside the expandable part 1, and then irradiation and hence therapy are carried out. Moreover, the structure is such that the radiation source tubular cavity 6 is closed in the catheter tip end direction, and hence the radiation source 16 does not come into direct contact with body fluid. FIG. 2 shows the state in which the radiation source 16 has been disposed inside the expandable part 11 in the case of the first example. FIG. 3 shows the expandable part 11 before expansion, and FIG. 4 shows the expandable part 11 after expansion. In the drawings, reference numeral 12 indicates the protruding parts, reference numeral 13 indicates the guide wire tubular cavity, reference numeral 14 indicates the guide wire entrance part, and reference numeral 15 indicates the guide wire exit part.

As shown in FIGS. 3 and 4, the expandable part comprises an inner layer 21 of relatively high elasticity and an outer layer 22 of relatively low elasticity, and the outer layer 22 has voids 23. Here, the relatively high elasticity and the relatively low elasticity means that the relative difference between the bend elastic constants as measured using a measurement method based on ASTM-D790 is at least 20%, and is as described earlier (likewise hereinafter). Moreover, inside the inner layer 21 there is an inner tube 24 that forms the radiation source tubular cavity 26. An inflation lumen 25 is formed between the inner layer 21 and the inner tube 24. The inflation lumen 25 communicates with the inflation port at the base end part of the catheter, and upon a surgeon carrying out an operation of introducing a contrast medium, physiological saline or the like into the expandable part 1 to apply pressure, the inner layer 21 expands, thus becoming the protruding parts 2. The inner layer 21 was made using a thermoplastic polyurethane elastomer E380 made by Nippon Miractran, and the outer layer 22 was made using a polyamide elastomer Pebax 7033 made by Atochem. The inner layer 21 and the outer layer 22 were joined together using a urethane adhesive UR0531 made by H. B. Fuller. The voids 23 provided in the outer layer 22 were made to have a diameter of 1.9 mm. The diameter of the voids 23 is not the diameter when looking from one direction at the void 23 existing on a curved surface, but rather is the diameter when the expandable part 1 is spread out so that the void 23 becomes planar. Moreover, the expandable part 1 was made such that the outside diameter before expansion was 1.50 mm. When the catheter was expanded with a pressure of 1.0 atm ($1.013 \times 10^5$ Pa), the outside diameter of the protruding parts 2 was 1.98 mm, and the outside diameter of parts where protruding parts 2 are not present was 1.52 mm. Moreover, when the catheter was expanded with a pressure of 2.0 atm ($2.027 \times 10^5$ Pa), the outside diameter of the protruding parts 2 was 2.63 mm, and the outside diameter of parts where protruding parts 2 are not present was 1.55 mm. Furthermore, when the catheter was expanded with a pressure of 3.0 atm ($3.040 \times 10^5$ Pa), the outside diameter of the protruding parts 2 was 3.30 mm, and the outside diameter of parts where protruding parts 2 are not present was 1.57 mm.

The following evaluation was carried out on the first example. Three mock blood vessels made of urethane and of inside diameter 2.5 mm, angle 180°, and radius of curvature 30 mm, 20 mm or 10 mm were prepared. The catheter of the first example was disposed in each mock blood vessel, and a pressure of 2.0 atm ($2.027 \times 10^5$ Pa) or 3.0 atm ($3.040 \times 10^5$ Pa) was applied to the catheter. For each of the above-mentioned mock blood vessels and each of the above-mentioned pressures, a mock radiation source was inserted into the radiation source tubular cavity 6, and it was verified that the mock radiation source was positioned in the center in the radial direction in all parts of the mock blood vessel. Moreover, physiological saline that had been colored red was made to flow into the mock blood vessel at a pressure difference of 16.0 kPa, and for each of the above-mentioned mock blood vessels and each of the above-mentioned pressures, it was verified that perfusion of the physiological saline occurred.

Figure 5:
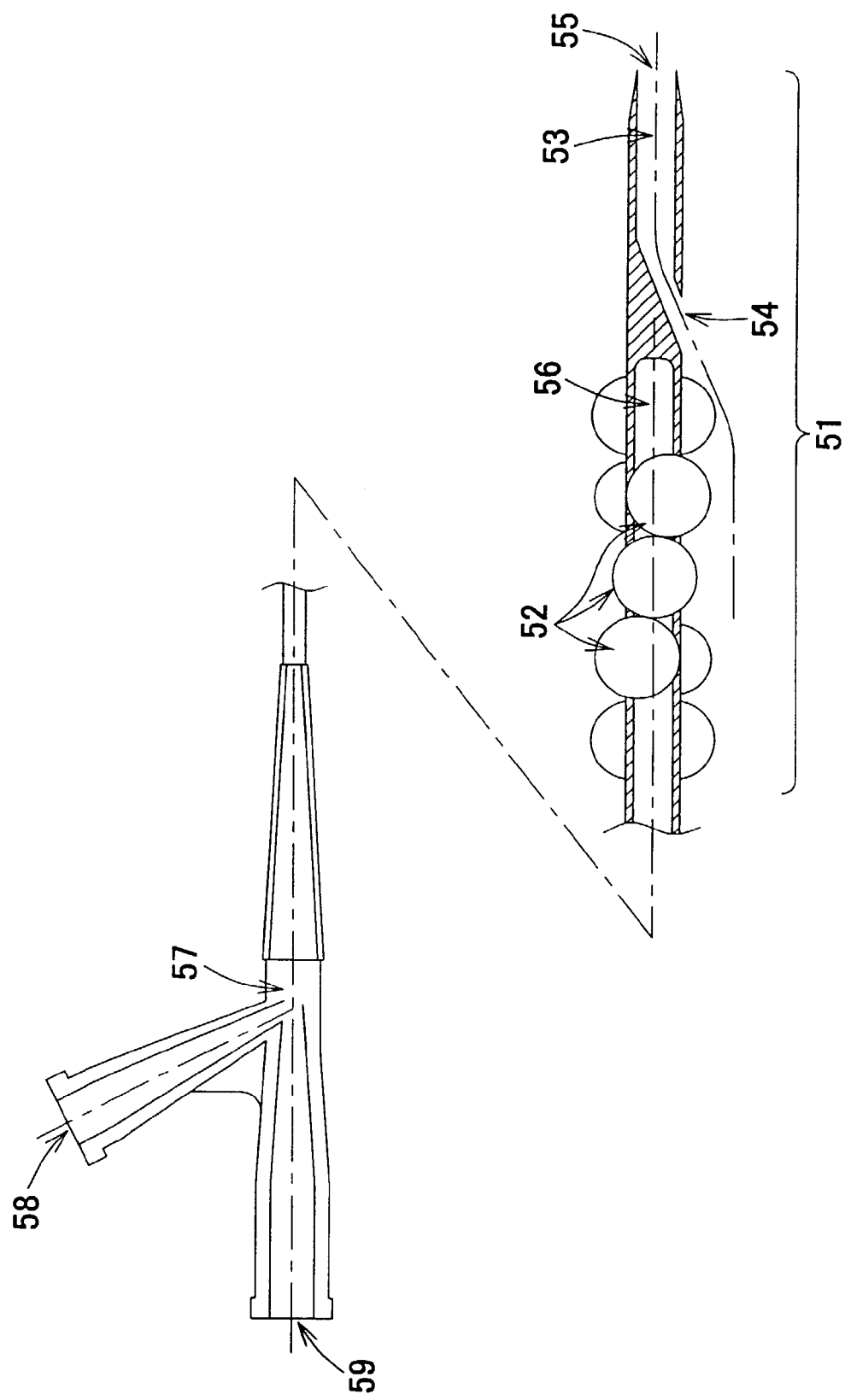
FIG. 5 is an axial direction sectional view of a second example.

A second example of FIG. 5 is a catheter for radiation therapy for treating part of a body vessel with ionizing radiation; a state in which the expandable part 51 has been expanded is shown. The expandable part 51 of the catheter is positioned on the tip end side of the catheter, and in the expanded state has a plurality of pairs of protruding parts 52. Specifically, when the expandable part 51 is expanded, a plurality of pairs of protruding parts 52 are produced, with the protruding parts 52 that constitute each pair being disposed so as to be produced facing in opposite directions to one another in a direction orthogonal to the axial direction of the expandable part 51, and moreover with pairs of protruding parts that are adjacent to one another in the axial direction being disposed in spiral fashion close to one another with an angle of less than 90° therebetween in the circumferential direction. In the example shown in the drawing, there are five pairs of protruding parts 52 in succession in the axial direction with angles of 45° between adjacent pairs, and hence the pairs of protruding parts 52 are formed in spiral fashion in the axial direction. Through the protruding parts 52, even in the case of a curved body vessel, a radiation source tubular cavity 56 is disposed in the center of the body vessel at all times, and hence irradiation can be carried out with a uniform dose.

Figure 6:
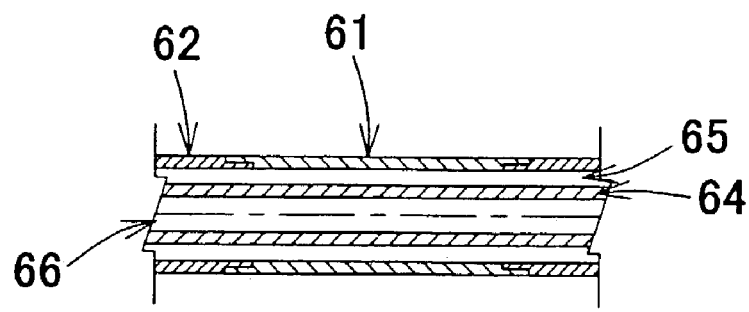
FIG. 6 shows the expandable part before expansion in the case of the second example.

The catheter has a guide wire tubular cavity 53, which is provided between a guide wire entrance part 54 and a guide wire exit part 55, with the guide wire entrance part 54 and the guide wire exit part 55 both being positioned on the tip end side relative to the expandable part 51. A manifold 57 is provided at a base end part of the catheter, and has an inflation port 58 and a radiation source port 59. The inflation port 58 communicates with the expandable part, and upon a surgeon carrying out an operation of introducing a contrast medium, physiological saline or the like into the expandable part 51 to apply pressure, the protruding parts 52 are produced on the expandable part 51. Note that when the expandable part 51 is contracted, the inflation port 58 becomes a deflation port. The radiation source port 59 communicates with the radiation source tubular cavity 56; a radiation source is inserted from the radiation source port 59 and is disposed inside the expandable part 51, and then irradiation and hence therapy are carried out. Moreover, the structure is such that the radiation source tubular cavity 56 is closed in the catheter tip end direction, and hence the radiation source does not come into direct contact with body fluid. FIG. 6 shows the expandable part 51 before expansion, and FIG. 7 shows the expandable part 51 after expansion.

Figure 7:
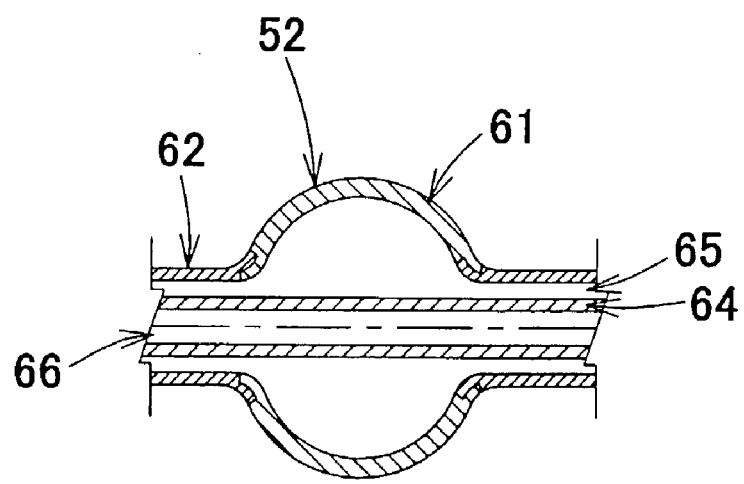
FIG. 7 shows the expandable part after expansion in the case of the second example.

As shown in FIGS. 6 and 7, the expandable part 51 is a tube comprising relatively-high-elasticity regions 61 and relatively-low-elasticity regions 62. Moreover, inside there is an inner tube 64 that forms the radiation source tubular cavity 66. An inflation lumen 65 is formed between the inner tube 64 and the tube comprising the relatively-high-elasticity regions 61 and the relatively-low-elasticity regions 62. The inflation lumen 65 communicates with the inflation port at the base end part of the catheter, and upon a surgeon carrying out an operation of introducing a contrast medium, physiological saline or the like into the expandable part 51 to apply pressure, the relatively-high-elasticity regions 61 expand, thus becoming the protruding parts 52. The relatively-high-elasticity regions 61 were made using a thermoplastic elastomer E380 made by Nippon Miractran, and the relatively-low-elasticity regions 62 were made using a thermoplastic elastomer E395 made by Nippon Miractran. Fabrication was carried out by dipping a tube made of E395 in which prescribed voids had been formed into a liquid of E380, wiping off the E380 attached to parts other than the parts where the voids were, and drying. The relatively-high-elasticity regions 61 were made to have a diameter of 1.0 mm. The diameter of the relatively-high-elasticity regions 61 is not the diameter when looking from one direction at the relatively-high-elasticity region 61 existing on a curved surface, but rather is the diameter when the expandable part is spread out so that the relatively-high-elasticity region 61 becomes planar. Moreover, the expandable part was made such that the outside diameter before expansion was 1.00 mm. When the catheter was expanded with a pressure of 1.0 atm ($1.013 \times 10^5$ Pa), the outside diameter of the protruding parts 52 was 1.25 mm, and the outside diameter of parts where protruding parts 52 are not present was 1.02 mm. Moreover, when the catheter was expanded with a pressure of 2.0 atm ($2.027 \times 10^5$ Pa), the outside diameter of the protruding parts 52 was 1.54 mm, and the outside diameter of parts where protruding parts 52 are not present was 1.03 mm. Furthermore, when the catheter was expanded with a pressure of 3.0 atm ($3.040 \times 10^5$ Pa), the outside diameter of the protruding parts 52 was 1.81 mm, and the outside diameter of parts where protruding parts 52 are not present was 1.06 mm.

The following evaluation was carried out on the second example. Three mock blood vessels made of urethane and of inside diameter 1.5 mm, angle 180°, and radius of curvature 30 mm, 20 mm or 10 mm were prepared. The catheter of the second example was disposed in each mock blood vessel, and a pressure of 2.0 atm ($2.027 \times 10^5$ Pa) or 3.0 atm ($3.040 \times 10^5$ Pa) was applied to the catheter. For each of the above-mentioned mock blood vessels and each of the above-mentioned pressures, a mock radiation source was inserted into the radiation source tubular cavity 66, and it was verified that the mock radiation source was positioned in the center in the radial direction in all parts of the mock blood vessel. Moreover, physiological saline that had been colored red was made to flow into the mock blood vessel at a pressure difference of 16.0 kPa, and for each of the above-mentioned mock blood vessels and each of the above-mentioned pressures, it was verified that perfusion of the physiological saline occurred.

Figure 8:
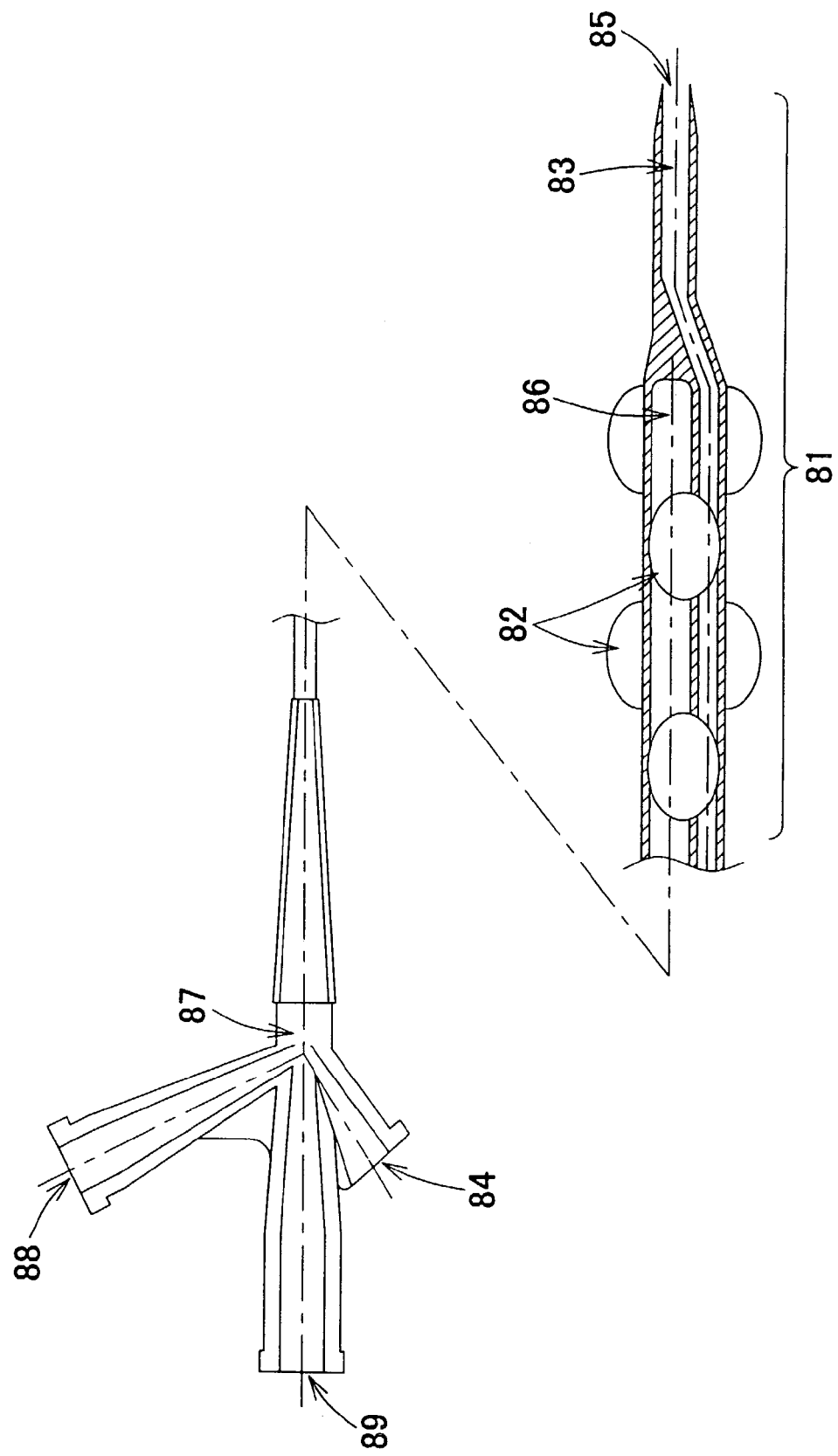
FIG. 8 is an axial direction sectional view of a third example.

A third example of FIG. 8 is a catheter for radiation therapy for treating part of a body vessel with ionizing radiation; a state in which the expandable part 81 has been expanded is shown. The expandable part 81 of the catheter is positioned on the tip end side of the catheter, and in the expanded state has a plurality of protruding parts 82. Specifically, when the expandable part 81 is expanded, a plurality of pairs of protruding parts 82 are produced, with the protruding parts 82 that constitute each pair being disposed so as to be produced facing in opposite directions to one another in a direction orthogonal to the axial direction of the expandable part 81, and moreover with pairs of protruding parts 82 that are adjacent to one another in the axial direction being disposed close to one another with an angle of 90° therebetween in the circumferential direction. In the example shown in the drawing, there are four pairs of protruding parts 82 in succession in the axial direction with angles of 90° between adjacent pairs, and hence the catheter of the third example has a total of eight protruding parts 82. Through the protruding parts 82, even in the case of a curved body vessel, a radiation source tubular cavity 86 is disposed in the center of the body vessel at all times, and hence irradiation can be carried out with a uniform dose. Moreover, the outline of each of the protruding parts 82 as viewed from the direction of protrusion of the protruding part 82 is elliptical. In other words, the shape of each of the protruding parts 82 is an ellipse that is long in the axial direction as viewed from the perpendicular direction of the protruding part 82 in the radial direction. By making the shape be an ellipse, the centering performance and the perfusion performance can be made to be better than in the case of a circular shape, and moreover the sliding ability of the catheter can be improved.

Figure 9:
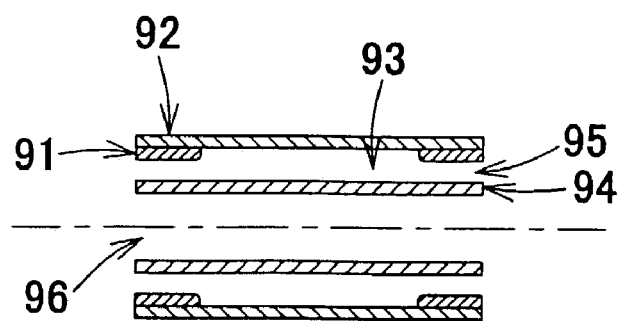
FIG. 9 shows the expandable part before expansion in the case of the third example.
Figure 10:
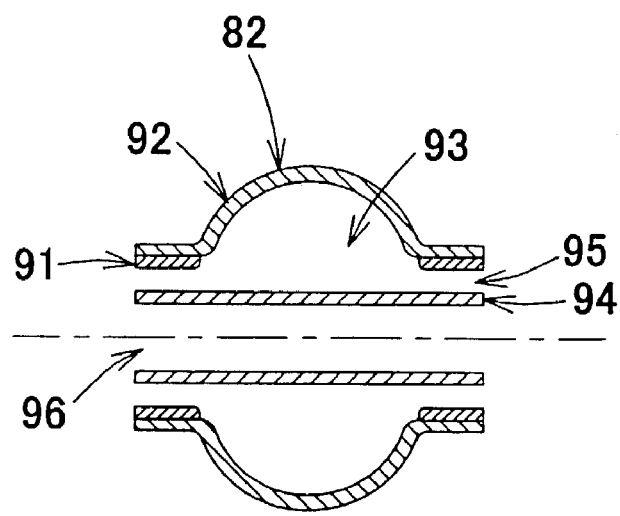
FIG. 10 shows the expandable part after expansion in the case of the third example.

The catheter has a guide wire tubular cavity 83, which is provided between a guide wire port 84 and a guide wire exit part 85, i.e. the guide wire tubular cavity is provided along the whole length of the catheter. A manifold 87 is provided at a base end part of the catheter, and has an inflation port 88, a radiation source port 89 and the guide wire port 84. The inflation port 88 communicates with the expandable part, and upon a surgeon carrying out an operation of introducing a contrast medium, physiological saline or the like into the expandable part 81 to apply pressure, the protruding parts 82 are produced on the expandable part 81. Note that when the expandable part 81 is contracted, the inflation port 88 becomes a deflation port. The radiation source port 89 communicates with the radiation source tubular cavity 86; a radiation source is inserted from the radiation source port 89 and is disposed inside the expandable part 81, and then irradiation and hence therapy are carried out. FIG. 9 shows the expandable part 81 before expansion, and FIG. 10 shows the expandable part 81 after expansion. The expandable part 81 comprises an inner layer 91 of relatively low elasticity and an outer layer 92 of relatively high elasticity, and the inner layer 91 has voids 93. Moreover, inside the inner layer 91 there is an inner tube 94 that forms the radiation source tubular cavity 96. An inflation lumen 95 is formed between the inner tube 94 and the tube constituted from the inner layer 91 and the outer layer 92. The inflation lumen 95 communicates with the inflation port at the base end part of the catheter, and upon a surgeon carrying out an operation of introducing a contrast medium, physiological saline or the like into the expandable part 81 to apply pressure, the outer layer 92 expands, thus becoming the protruding parts 82.

The inner layer 91 was made using a polyamide elastomer Pebax 7033 made by Atochem, and the outer layer 92 was made using a thermoplastic polyurethane elastomer E380 made by Nippon Miractran. The inner layer 91 and the outer layer 92 were joined together using a urethane adhesive UR0531 made by H. B. Fuller. The voids 93 provided in the inner layer 91 were made to have a short diameter of 1.0 mm, and a long diameter of 1.4 mm. The short diameter and the long diameter of the voids 93 are not the short diameter and the long diameter when looking from one direction at the void 93 existing on a curved surface, but rather are the short diameter and the long diameter when the expandable part 81 is spread out so that the void 93 becomes planar. Moreover, the expandable part 81 was made such that the outside diameter before expansion was 1.25 mm. When the catheter was expanded with a pressure of 1.0 atm ($1.013 \times 10^5$ Pa), the outside diameter of the protruding parts 82 was 1.58 mm, and the outside diameter of parts where protruding parts 82 are not present was 1.26 mm. Moreover, when the catheter was expanded with a pressure of 2.0 atm ($2.027 \times 10^5$ Pa), the outside diameter of the protruding parts 82 was 2.02 mm, and the outside diameter of parts where protruding parts 82 are not present was 1.28 mm. Furthermore, when the catheter was expanded with a pressure of 3.0 atm ($3.040 \times 10^5$ Pa), the outside diameter of the protruding parts 82 was 2.47 mm, and the outside diameter of parts where protruding parts 82 are not present was 1.31 mm.

The following evaluation was carried out on the third example. Three mock blood vessels made of urethane and of inside diameter 2.0 mm, angle 180°, and radius of curvature 30 mm, 20 mm or 10 mm were prepared. The catheter of the third example was disposed in each mock blood vessel, and a pressure of 2.0 atm ($2.027 \times 10^5$ Pa) or 3.0 atm ($3.040 \times 10^5$ Pa) was applied to the catheter. For each of the above-mentioned mock blood vessels and each of the above-mentioned pressures, a mock radiation source was inserted into the radiation source tubular cavity 96, and it was verified that the mock radiation source was positioned in the center in the radial direction in all parts of the mock blood vessel. Moreover, physiological saline that had been colored red was made to flow into the mock blood vessel at a pressure difference of 16.0 kPa, and for each of the above-mentioned mock blood vessels and each of the above-mentioned pressures, it was verified that perfusion of the physiological saline occurred.

INDUSTRIAL APPLICABILITY

By adopting a structure as in the present invention in which a part that expands comprises two materials having a different elasticity to one another, and due to this elasticity difference, the part that expands has a surface with no level differences thereon when not expanded, but when expanded high-elasticity parts in specific regions expand to produce protruding parts, a radiation source can be positioned in the central part of a blood vessel at all times, perfusion of a body fluid is possible, and moreover because the outer surface has no undulations, the risk of the inner walls of the blood vessel being damaged is reduced.

The invention claimed is:

1. A catheter for radiation therapy for treating part of a body vessel with ionizing radiation, the catheter for radiation therapy having a long catheter having a tip end part and a base end part, comprising an expandable part positioned on the tip end side of said catheter, and means for passing a radiation source through said catheter in a longitudinal direction to dispose said radiation source in said expandable part, wherein said expandable part has a two-layer structure in a radial direction of an inner layer and an outer layer, at least the inner layer is formed from an elastic substance, the bend elastic constant as measured using a measurement method based on ASTM-D790 is set to be at least 20% higher for the outer layer than for the inner layer, one or a plurality of voids are present in said outer layer, said expandable part has no protruding parts on the surface thereof when not expanded, and parts of the inner layer protrude from said voids of said outer layer when said expandable part is expanded, whereby when said expandable part is expanded, perfusion of a body fluid in the vicinity of said expandable part is made possible, and the protruding parts of said expandable part are disposed such that, when a radiation source is disposed inside the expandable part, the radiation source is always positioned in the center of said expandable part in the radial direction.

2. A catheter for radiation therapy for treating part of a body vessel with ionizing radiation, the catheter for radiation therapy having a long catheter having a tip end part and a base end part, comprising an expandable part positioned on the tip end side of said catheter, and means for passing a radiation source through said catheter in a longitudinal direction to dispose said radiation source in said expandable part, wherein said expandable part has high-elasticity regions and low-elasticity regions, the bend elastic constant as measured using a measurement method based on ASTM-D790 is set to be at least 20% higher for the low-elasticity regions than for the high-elasticity regions, said expandable part has no protruding parts on the surface thereof when not expanded, and one or a plurality of protruding parts are produced at said high-elasticity regions when said expandable part is expanded, whereby when said expandable part is expanded, perfusion of a body fluid in the vicinity of said expandable part is made possible, and the protruding parts of said expandable part are disposed such that, when a radiation source is disposed inside the expandable part, the radiation source is always positioned in the center of said expandable part in the radial direction.

3. A catheter for radiation therapy for treating part of a body vessel with ionizing radiation, the catheter for radiation therapy having a long catheter having a tip end part and a base end part, comprising an expandable part positioned on the tip end side of said catheter, and means for passing a radiation source through said catheter in a longitudinal direction to dispose said radiation source in said expandable part, wherein said expandable part has a two-layer structure in a radial direction of an inner layer and an outer layer both formed from an elastic substance, the bend elastic constant as measured using a measurement method based on ASTM-D790 is set to be at least 20% higher for the inner layer than for the outer layer, one or a plurality of voids are present in said inner layer, said expandable part has no protruding parts on the surface thereof when not expanded, and parts of the outer layer corresponding to parts where said voids are present in said inner layer protrude when said expandable part is expanded, whereby when said expandable part is expanded, perfusion of a body fluid in the vicinity of said expandable part is made possible, and the protruding parts of said expandable part are disposed such that, when a radiation source is disposed inside the expandable part, the radiation source is always positioned in the center of said expandable part in the radial direction.

4. The catheter for radiation therapy according to any of claims 1 through 3, having a guide wire tubular cavity, wherein said tubular cavity is provided only on the tip end side relative to the expandable part.

5. The catheter for radiation therapy according to any of claims 1 through 3, wherein when said expandable part is expanded, one or a plurality of pairs of protruding parts are produced, and the protruding parts that constitute each pair are disposed so as to be produced facing in opposite directions to one another in a direction orthogonal to the axial direction of said expandable part.

6. The catheter for radiation therapy according to any of claims 1 through 3, wherein when said expandable part is expanded, a plurality of pairs of protruding parts are produced, with the protruding parts that constitute each pair being disposed so as to be produced facing in opposite directions to one another in a direction orthogonal to the axial direction of said expandable part, and with pairs of protruding parts that are adjacent to one another in the axial direction being disposed close to one another with an angle of 90° therebetween in the circumferential direction.

7. The catheter for radiation therapy according to any of claims 1 through 3, wherein when said expandable part is expanded, a plurality of pairs of protruding parts are produced, with the protruding parts that constitute each pair being disposed so as to be produced facing in opposite directions to one another in a direction orthogonal to the axial direction of said expandable part, and with pairs of protruding parts that are adjacent to one another in the axial direction being disposed in spiral fashion close to one another with an angle of less than 90° therebetween in the circumferential direction.

8. The catheter for radiation therapy according to any of claims 1 through 3, wherein the outline of said protruding parts as viewed from the direction of protrusion of said protruding parts is approximately circular.

9. The catheter for radiation therapy according to any of claims 1 through 3, wherein the outline of said protruding parts as viewed from the direction of protrusion of said protruding parts is elliptical.

10. The catheter for radiation therapy according to any of claims 1 through 3, wherein the material of high-elasticity parts having a low bend elastic constant and the material of low-elasticity parts having a high bend elastic constant of the expandable part are resins selected from out of polyurethanes, urethane type elastomers, polyamides, polyamide type elastomers, polyester type resins, polyester elastomers, olefin type resins, olefin type elastomers, polystyrene, styrene type elastomers, vinyl chloride, vinyl chloride type elastomers, silicones, natural rubber, and synthetic rubbers.

11. The catheter for radiation therapy according to claim 1, wherein the material of the outer layer of the expandable part is a metal.

12. The catheter for radiation therapy according to any of claims 1 through 3, wherein the outside diameter expansion rate per unit expansion pressure is at least 25.0%/atm (0.247%/kPa) in regions where protruding parts are produced, and not more than 2.5%/atm (0.0247%/kPa) in regions where protruding parts are not produced.

* * * * *